United States Patent [19]

Schueller et al.

[11] Patent Number: 5,306,434
[45] Date of Patent: Apr. 26, 1994

[54] HAIR CARE COMPOSITION CONTAINING DISPERSED SILICONE OIL

[75] Inventors: Randy M. Schueller, Park Ridge; Gilles M. L. Verboom, Mundelein; Sheila M. Moran, Palatine; Barry W. Williams, Country Club Hills, all of Ill.

[73] Assignee: Alberto-Culver Company, Melrose Park, Ill.

[21] Appl. No.: 963,603

[22] Filed: Oct. 20, 1992

[51] Int. Cl.⁵ .................. C11D 3/12; C11D 3/37; A61K 7/08; A61K 7/06
[52] U.S. Cl. ........................ 252/8.8; 252/8.6; 252/174.15; 252/174.23; 252/DIG. 13; 424/70
[58] Field of Search ............ 424/70; 252/174.15, 252/174.23, DIG. 13, 8.8, 8.6

[56] References Cited

U.S. PATENT DOCUMENTS

| | | | |
|---|---|---|---|
| 3,964,500 | 6/1976 | Drakoff | 132/7 |
| 4,387,090 | 6/1983 | Bolich, Jr. | 424/70 |
| 4,529,586 | 7/1985 | De Marco et al. | 424/70 |
| 4,597,962 | 7/1986 | Grollier et al. | 424/47 |
| 4,704,272 | 11/1987 | Oh et al. | 424/70 |
| 4,839,167 | 6/1989 | Yamamoto et al. | 424/71 |
| 4,891,166 | 1/1990 | Schaefer et al. | 260/404.5 |
| 4,983,383 | 1/1991 | Maksimoski et al. | 424/70 |
| 5,034,218 | 7/1991 | Duvel | 424/70 |
| 5,049,377 | 9/1991 | Lamb et al. | 424/70 |
| 5,077,040 | 12/1991 | Bergman et al. | 424/70 |
| 5,078,990 | 1/1992 | Martin et al. | 424/70 |
| 5,126,126 | 6/1992 | Varapath et al. | 424/71 |
| 5,169,622 | 12/1992 | Kopolow et al. | 424/47 |

OTHER PUBLICATIONS

Sacklowski, Helga Organo modified polydimethylsiloxanes in hair preparations. Seifen, Oele, Fette, Wache 115(17), 607–12 Oct. 31, 1989.

*Primary Examiner*—Paul Lieberman
*Assistant Examiner*—Michael P. Tierney
*Attorney, Agent, or Firm*—Tilton, Fallon, Lungmus & Chestnut

[57] ABSTRACT

Hair care compositions are provided in which a silicone oil is dispersed in water by the action of a diquaternary polydimethylsiloxane. Polyvinylpyrrolidone may be included as a co-dispersant/stabilizer. The dispersed silicone oil combination is useful in hair conditioner formulations.

3 Claims, No Drawings

HAIR CARE COMPOSITION CONTAINING DISPERSED SILICONE OIL

FIELD OF INVENTION

The field of this invention is hair care compositions containing hair conditioners. More particularly, this invention relates to aqueous hair conditioning compositions containing silicone oil.

BACKGROUND OF INVENTION

In accordance with hair composition terminology, the term "silicone oil" is used herein to designate water-insoluble silicone polymers which are applied to hair to improve its feel or appearance. Silicone oils can provide the hair with a silky, lubricious feel. They can also provide a lusterization effect. These results are obtained by coating hair strands with thin films of silicone oil.

Since silicone oils are substantially water-insoluble, after application to the hair they tend to remain thereon despite rinsing with water. Silicone oil can therefore be applied in a shampoo, or in a hair conditioner applied after shampooing, and then followed by water-rinsing.

The two most common types of hair conditioning silicone oils are referred to in the International Cosmetic Ingredient Dictionary (CTFA) as "dimethicone" and "dimethiconol". Dimethicone is defined as a mixture of fully methylated linear siloxane polymers end blocked with trimethylsiloxy units. Dimethiconol is a dimethyl silicone polymer terminated with hydroxyl groups. Such hair conditioning silicone oils are relatively non-volatile liquids. Dimethicone and dimethiconol silicone oils are obtainable from commercial sources in the United States and other countries.

Since silicone oils have very limited solubility in aqueous products, they are usually applied in the form of aqueous emulsions or dispersions. For example, in a water-based shampoo or hair conditioner, the silicone oil may be dispersed with the aid of an emulsifying agent, and the dispersion or emulsion may be stabilized by the inclusion of thickeners.

Cationic hair conditioning agents are also commonly used in hair treating compositions. Typically, cationic hair conditioning agents contain one or more cationic quaternary nitrogen groups, and one or more hydrophobic long chain aliphatic or silicone polymer. The cationic group can provide a degree of substantivity between the conditioning agent and hair. The long chain hydrophobic groups, which are derived from long chain fatty acids, or are silicone polymers, can provide hair conditioning functions.

Silicone oils have been disclosed as ingredients of water-based shampoos which also contain a quaternary nitrogen-containing conditioning agent and an anionic surfactant. U.S. Pat. Nos. 4,704,272, 3,964,500, and 5,034,218 are illustrative of such formulations. Silicone oils are also disclosed as ingredients of after-shampoo hair conditioning emulsions. (See, for example, U.S. Pat. No. 4,387,090.)

Silicone co-polymers, designated by the CTFA as "dimethicone copolyol" are also used in hair conditioner compositions. The cosmetic Dictionary definition is: a polymer of dimethylpolysiloxane with polyoxyethylene and/or polyoxypropylene side chains. These copolymers are not silicone oils since they are water-soluble.

Cationic silicone polymers have been proposed for use in hair conditioning compositions, as disclosed in U.S. Pat. Nos. 4,529,586, 4,597,962 and 4,839,167. U.S. Pat. No. 4,529,586 describes a hair conditioning composition in which one of the ingredients is an amino functional silicone polymer. The composition also contains a cationic surfactant-emulsifier and a cationic polymer.

U.S. Pat. No. 4,597,962 discloses compositions containing cationic silicone polymers of specified structural formulas. The compositions also include a cationic surface-active agent and a water-soluble diquaternary polyammonium compound.

U.S. Pat. No. 4,839,167 discloses an emulsion-type hair cosmetic containing a dimethylpolysiloxane polyoxyalkylene copolymer. The compositions also contain dimethicone copolyol, and the compositions are formulated from mixtures of water and ethanol. In the compositions of the previously cited patents (U.S. Pat. Nos. 4,529,586 and 4,597,962) water is used as the carrier.

SUMMARY OF INVENTION

This invention is based in part on the discovery that certain diquaternary dimethylpolysiloxanes can act as a primary dispersant or solubilizing agent for silicone oil in an aqueous carrier. This discovery facilitates preparation of hair care compositions which contain silicone oil in aqueous admixture with quaternary hair conditioning agents. Other commercially available quaternary hair conditioning agents are not effective for dispersion of silicone oil in water. In the compositions of this invention, diquaternary polydimethylsiloxanes perform a double function, acting not only as cationic hair conditioners, but also and importantly as a dispersing agent for a silicone oil conditioner. These compositions can thereby effectively combine the conditioning properties of silicone oil and the diquaternary polydimethylsiloxane.

In the development of this invention, it was further discovered to be desirable to incorporate polyvinylpyrrolidone (PVP) in the formulations. More specifically, it appears that PVP acts as a co-dispersant for silicone oil. Consequently, when PVP is used in combination with certain diquaternary polydimethyl-siloxanes, smaller concentrations of each of these ingredients can be employed to effectively disperse a given amount of silicone oil, or more silicone oil can be dispersed with the same concentration of the diquaternary dispersant.

The composition of the present invention are preferably formulated as dilute aqueous dispersions. For example, the combination of the silicone oil, diquaternary, and PVP may comprise together from 1 to 44 by weight of the formulation. Other water-soluble or emulsifiable hair treating agents can be included, such as dimethicone copolyol, glycerine, cetyl alcohol, stearyl alcohol, glyceryl stearate, stearamidopropyl dimethylamine, dimethicone copolyol sulfosuccinate, etc. Complete formulations with such added ingredients may be produced with part of the ingredients in aqueous solution and other ingredients dispersed as a stable emulsion.

DETAILED DESCRIPTION

The hair care compositions of this invention are formulated in a water carrier. On a weight percent basis, the water may comprise from 70 to 95% of the total composition. In some preferred embodiments, the compositions can contain from about 85 to 95% by weight water.

Silicone oil is a key ingredient. The aqueous compositions can contain from 0.2 to 2.0 weight percent silicone oil. In other embodiments, they will contain from 0.5 to 1.5 weight percent silicone oil. Such water-insoluble, non-volatile silicone oils (also sometimes called silicone fluids) are well known in the cosmetic arts, and are available through a number of commercial sources in the United States and other countries. They are referred to in the International Cosmetic Dictionary (CTFA) as "dimethicone" and "dimethiconol". They are also described in the patent literature. For example, reference may be had to U.S. Pat. No. 4,704,272, and the description of non-volatile silicone fluids found in columns 4 and 5 thereof. Such silicone oils or fluids can be obtained in the United States from the Dow Corning Corporation, Midland, Mich., and other companies such as Mazer Chemicals, Gurnee, Ill. Typically, these products have viscosities of 10,000 to 60,000 cps.

For dispersing the silicone oil in the water carrier in accordance with the present invention it is essential to employ a diquaternary polydimethylsiloxane which can function as an effective dispersant/emulsifier for silicone oils. It is believed that such diquaternary compounds can have an average molecular weight in the range from 1000 to 4000, and that they may contain siloxane chains in the range from 5 to 40 dimethylsiloxy units. These diquaternary compounds, suitable for use in the formulations of this invention, can have the following formula:

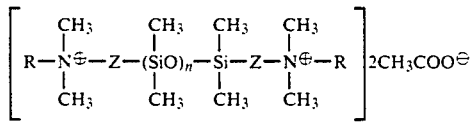

wherein Z is the

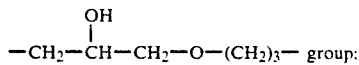 group:

n is a number from 5 to 40, or preferably 25 to 35, and both R's are short chain alkyl groups containing from 2 to 8 carbons, or preferably 4 to 6 carbons.

While the molecular weight of these compounds can range from 1000 to 4000, in preferred embodiments the average molecular weight is in the range from 2500 to 3500. Such a diquaternary polydimethylsiloxane is available from Goldschmidt AG, Essen, Germany, as "ABIL-Quat" 3272. It's understood to have an average molecular weight of around 3000, a siloxane chain containing an average of 30 dimethylsiloxy units, and short chain alkyl groups containing 5 carbons. "ABIL-Quat" 3270 is another diquaternary polydimethylsiloxane available from Goldschmidt. While it can be used for the purposes of this invention, it is less preferred for dispersing silicone oil. The 3270 compound is understood to have an average molecular weight of about 1500, a siloxane chain containing an average of 10 dimethylsiloxy units, and short chain alkyl groups of 5 carbon length.

Diquaternary dimethylpolysiloxanes of the general kind usable in the compositions of the present invention have been assigned the CTFA generic name "Quaternium 80". Unfortunately, however, the initial listing under this designation in the CTFA Cosmetic Ingredients Dictionary contains an incorrect representation of the structural formula, showing a structure having a quaternary ammonium group together with an amido amine group rather than two quaternary ammonium groups. Other diquaternary dimethylpolysiloxane compounds which can be used in the compositions of the present invention can be prepared as described in U.S. Pat. No. 4,891,166, which is issued to Goldschmidt AG.

For emulsifying the amounts of silicone oil in water as referred to above, correspondingly small amounts of the diquaternary dispersant can be used. For example, the amount required may range from 0.1 to 1.5 weight percent of the hair conditioning composition, or in preferred embodiments from 0.2 to 1.0 weight percent. When operating within these ranges, it will be understood that the amount of the diquaternary to be employed should be sufficient to disperse the amount of silicone oil. For example, when water is mixed with 1% dimethicone, the insoluble dimethicone will form a distinct layer on top of the water. However, the addition of as little as 0.25% of the product identified by the trademark "ABIL-Quat" 3272 will induce the dispersal of the dimethicone, resulting in a milky opacity showing that a dispersion/emulsion has been formed. As the amount of the diquaternary dispersant is increased, an increasingly complete dispersion is achieved. For example, this can be achieved at a level of 1.0% of the diquaternary which is sufficient to disperse 1.0% of the dimethicone.

Dispersal of the silicone oil by the action of the diquaternary appears to be assisted by the inclusion of a small amount of polyvinylpyrrolidone (PVP). For example, the amount of PVP used may range from 0.1 to 2.0% by weight of the total composition. In preferred embodiments, the amount of PVP is within the range from 0.5 to 1.5 weight percent of the total composition. PVP is available commercially with various average chain lengths. In general, for purposes of the present invention, the PVP can have an average molecular weight in the range from 10,000 to 100,000. In preferred embodiments, a PVP is selected which has a molecular weight in the range from 20,000 to 60,000. For example, a suitable PVP is obtainable from ISP Corporation, Wayne, N.J. being sold as "PVP K-30". The designation "30" is understood to indicate that the average molecular weight is approximately 30,000.

For combining the principal ingredients of the compositions of this invention, the following formulation instructions can be used as a guide.

Formulation Instructions

| Ingredients | Parts by Weight | |
| --- | --- | --- |
| | Broad | Preferred |
| Water | 70-95 | 85-95 |
| Silicone Oil[a] | 0.2-2.0 | 0.5-1.5 |
| Diquaternary Polydimethylsiloxane[b] | 0.1-1.5 | 0.2-1.0 |
| PVP[c] | 0.1-2.0 | 0.5-1.5 |

[a]Dimethicone and/or dimethiconol polymer.
[b]"ABIL-Quat" 3272 or 3270, trademarked products of Goldschmidt AG.
[c]Molecular weight 20,000-60,000, viz. "PVP-K-30", ISP Corp. (formerly GAF Corp.)

As is well known in the cosmetic arts, complete hair conditioning formulations may include small amounts of many other compounds which can contribute to the overall performance of the product. An illustrative complete formulation is set out below.

Illustrative Formulation

| Ingredients | Weight Percent |
|---|---|
| Water | 89.13 |
| FD&C Blue No. 1 | 0.00000 |
| Glycerin | 1.00 |
| Citric Acid | 0.17 |
| Polyvinylpyrrolidone [a] | 1.00 |
| Hydroxyethylcellulose [b] | 0.70 |
| Quaternium-18 [c] | 1.50 |
| Diquaternary polydimethylsiloxane [d] | 0.30 |
| Cetyl Alcohol | 2.00 |
| Stearyl Alcohol | 0.70 |
| Steareth-21 | 0.30 |
| Glyceryl Stearate | 0.30 |
| Stearamidopropyl Dimethylamine | 0.50 |
| Dimethicone [e] | 0.90 |
| Oleamine Oxide | 0.40 |
| Dimethicone Copolyol [f] | 0.30 |
| Disodium Dimethicone Copolyol Sulfosuccinate [g] | 0.20 |
| DMDM Hydantoin | 0.20 |
| Fragrance | 0.40 |
| | 100.00 |

[a] PVP K-30, ISP Corp.
[b] Water-soluble cellulose ether.
[c] Dimethyl dihydrogenated tallow ammonium chloride.
[d] "ABIL-Quat" 3272, trademarked product of Goldschmidt AG.
[e] Dimethyl polysiloxane. (Av. mol. wt. 60,000). "Masil" SF 60,000 trademarked product of Mazer Chemicals; or dimethicone/dimethiconol, Fluid Q2-1403, trademarked product of Dow Corning.
[f] Dow Corning 193 Surfactant.
[g] "Mackanate" DC-30, trademarked product of McIntyre Group, Ltd., Chicago, Illinois.

A presently preferred manufacturing procedure for producing the above product is as follows:

Manufacturing Procedure (1) Equip manufacturing vessel with appropriate mixing apparatus (e.g., Lightnin' Mixer) and charge with water.

(2) With moderate agitation disperse the PVP, FD&C blue dye, glycerine, hydroxyethylcellulose and citric acid. Continue mixing until homogeneous.

(3) Begin heating and add Quaternium 18. Mix until smooth (at 150° F.).

(4) At 160° F. add cetyl and stearyl alcohols, the Steareth-21 and the glyceryl monostearate. Continue heating to 177° F.; continue mixing at this temperature for 30 minutes.

(5) Premix dimethicone and the diquaternary polydimethylsiloxane.

(6) Reduce heat; at 165° F. add mixture to batch. Continue mixing at this temperature for 30-60 minutes.

(7) Start cooling.

(8) At 130° F. add remaining ingredients.

The product as described above is designed for use as an after-shampoo conditioner. Following shampooing with the hair still wet, a small amount of the hair conditioner is applied and massaged into the hair. Thereafter, the hair is rinsed in the usual way. After drying, the hair is found to be free of objectionable residue and to exhibit an almost glass-like feel. This provides a very effective conditioning action without leaving the hair feeling objectionably coated, limp or dirty.

We claim:

1. An after-shampoo hair conditioner composition comprising an aqueous dispersion of a water-insoluble hair-conditioning silicone oil having a viscosity of from 10,000 to 60,000 cps and being present in an amount of 0.20 to 2.0% by weight of the composition, said composition containing a dispersing agent for said silicone oil consisting of 0.1 to 1.5% of a diquaternary polydimethylsiloxane having an average molecular weight from 1000 to 4000, said polydimethylsiloxane having the diquaternary structure of the formula:

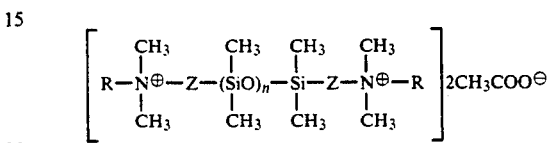

wherein Z is

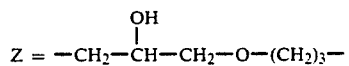

and n is a number from 5 to 40 and both R's are an alkyl group containing from 4 to 6 carbons.

2. The hair conditioning composition of claim 1 in which said composition contains from 0.5 to 1.5% of said silicone oil and from 0.2 to 1.0% of said diquaternary polydimethylsiloxane.

3. An after-shampoo hair conditioner composition comprising a stable emulsion containing 85 to 95% water, 0.5 to 1.5% of a water-insoluble hair-conditioning silicone oil, and 0.2 to 1.0% of a diquaternary polydimethylsiloxane dispersing agent for the silicone oil, said percentages being based on the weight of the composition, said silicone oil having a viscosity of 10,000 to 60,000 cps, and said polydimethylsiloxane having an average molecular weight from 2500 to 3500, said polydimethylsiloxane having the diquaternary structure of the formula:

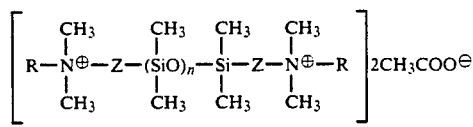

wherein Z is

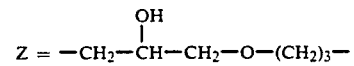

and n is a number from 25 to 35 and both R's are an alkyl group containing from 4 to 6 carbons.

* * * * *